United States Patent [19]
Brackett

[11] Patent Number: 5,868,250
[45] Date of Patent: Feb. 9, 1999

[54] TRAY FOR HOLDING MEDICAL INSTRUMENTS

[76] Inventor: Fred Brackett, 8255 Brackett La., Semmes, Ala. 36575

[21] Appl. No.: 935,835

[22] Filed: Sep. 23, 1997

Related U.S. Application Data

[60] Provisional application No. 60/026,728, Sep. 26, 1996.
[51] Int. Cl.[6] .................................................. B65D 83/10
[52] U.S. Cl. ......................... 206/363; 206/370; 206/438
[58] Field of Search ..................................... 206/366, 369, 206/370, 363, 459.5, 438, 562

[56] References Cited

U.S. PATENT DOCUMENTS

| | | | |
|---|---|---|---|
| 4,349,338 | 9/1982 | Heppler | 206/459.5 |
| 4,420,085 | 12/1983 | Wilson et al. | 206/370 |
| 4,844,249 | 7/1989 | Coulombe | 206/438 |
| 5,007,535 | 4/1991 | Meseke et al. | 206/366 |
| 5,024,326 | 6/1991 | Sandel | 206/370 |
| 5,067,949 | 11/1991 | Freundlich et al. | 206/366 |
| 5,469,964 | 11/1995 | Bailey | 206/370 |
| 5,624,412 | 4/1997 | Weekley | 206/370 |
| 5,626,227 | 5/1997 | Wagner et al. | 206/369 |
| 5,628,400 | 5/1997 | Feder | 206/379 |

*Primary Examiner*—David T. Fidel

[57] ABSTRACT

A tray for dispensing and receiving surgical equipment having a series of holders attached to a tray fitted with needle caps, needles, syringes, scalpel covers, scalpel, and other such components. The system uses a bar with a locking mechanism which would allow the bar and other components to move from a plane horizontal to the base of the tray to a position raised above the walls of tray and in a staggered formation. The holding mechanism also allows for bathing the instruments in an antiseptic solution. The sharp components may be removed from rest of the tray in a covered condition for separate disposal. The bar is interspersed with a sponge like material for absorbing fluids, to cushion the return of medical devices and for holding components. The holders may be designed to guide the sharp component into its respective holder. Color or shape coding may be used to assist the return of a device to its specified holder (e.g. scalpels to the scalpel holder, needles on syringe to needle holders.

27 Claims, 5 Drawing Sheets

TRAY FOR HOLDING MEDICAL INSTRUMENTS

PRIORITY

This patent is a continuation in part of the provisional U.S. Pat. No. 60/026,728 filed Sep. 26, 1996.

BACKGROUND OF INVENTION

This invention applies to medical trays. More particularly, the invention applies to medical trays having a holding mechanism for holding medical devices.

PRIOR ART

Several trays are manufactured for dispensing components from a tray with a horizontal bar having a series of holding means for holding the medical devices. Improvements to some medical device holders include horizontal rests to hold the medical devices, but not the holding means for holding the devices, at a single elevated position, sponges for absorbing fluids and molding in such a fashion as to form multi-channeled or grooved bottoms in which syringes, needles, scalpels and other components lie loosely in. For example, the 662 patent, shows a non-tray oriented medical holding means where a rod is present which is neither staggered nor in contact with the holding means. The holding means in the current invention is deeper to allow the instruments to rest unencumbered within the tray when not in use. To retrieve a component from existing trays, one would reach into the bottom of the tray and retrieve the component which is lying loosely in the channel or groove. Thereafter, the user must remove the needle cover or other component cover and use the component. One problem associated with these trays is what to do with the component after the first use. Often a component is used more than once. Also, at times needles and syringes are placed in the tray bottoms after unsuccessful attempts to place lines and other medical devices only to be re-united again for another attempt to place these devices. The risk of injury to medical personnel increases with each additional attempt as blood from the patient is now within or on the needles, syringes, scalpels, other components and even in the tray bottom.

Therefore, it is the purpose of this invention to provide a safer, orderly dispensing system for components from medical trays.

A further purpose is to provide a safe way to re-cap needles and scalpels on medical trays, therefore making it safer to retrieve components from trays after they become contaminated with patients' blood.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein:

SUMMARY OF THE INVENTION

The invention is an improved orderly and safer way to dispense, retrieve, and dispose of components after use from medical trays. The system consists of a movable bar. The bar receives the medical components. The bar swivels so that the components held by the bar may be swivelled up to raised or lower the components from the tray bottom. The bar may lock in place (raised or lowered) with a locking mechanism to raise or lower the components from the tray bottom. The bar retains the covers for the components so they can be safely dispensed and returned after use. The covers have locking mechanisms (or needle caps) for components as a safe-guard against unintentional dislodgement. The bar may also contain sponge between components for quick and easy temporary storage for components. The entire bar and its components can be disengaged from tray and disposed of in one unit.

The bar lock may be described as follows a lock which restricts frictionally the movement of the bar holding the syringes.

The bar swivel may be described as follows: a bar rotatably mounted onto sides of a tray. In this way as the bar swivels, items mounted on the bar are raised out of the tray or lowered back into the tray.

A retaining means is described as as holes in the bar. The needle covers are caps screw into these holes in the bar. This allows the user to use only one hand to recap the needles.

The cover locking mechanism or needle caps fasten to the bar in the manner described.

The function of the sponge may be described as follows :The sponge may receive the needle. There is a face of the sponge which is exposed to receive the needle. The rest of the sponge may be covered. The presence of sponge or styrofoam in a cup is present in the prior art.

BRIEF DESCRIPTION OF THE DRAWINGS

Figure 1:
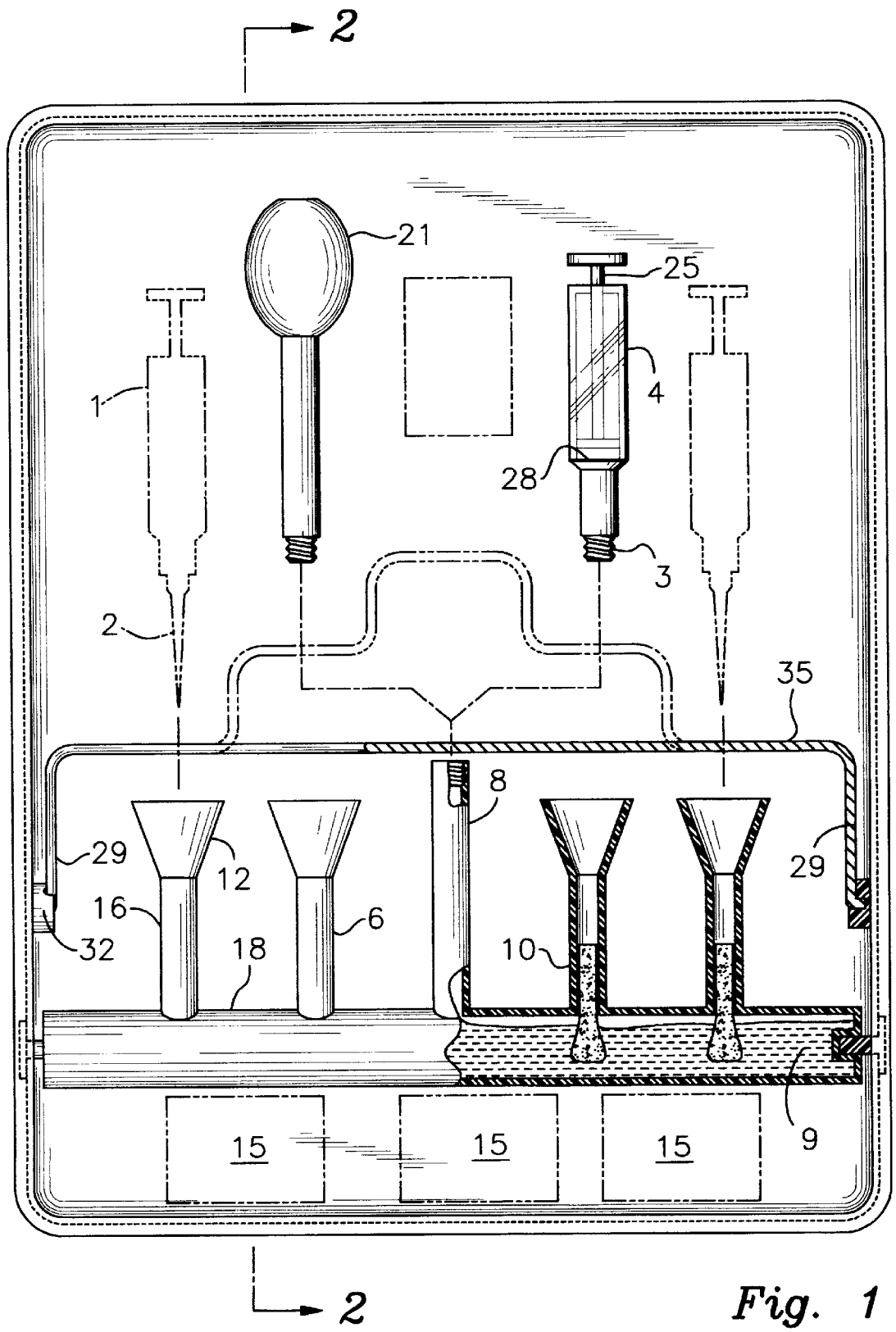

FIG. 1 is a plan view of the preferred embodiment.

Figure 2:
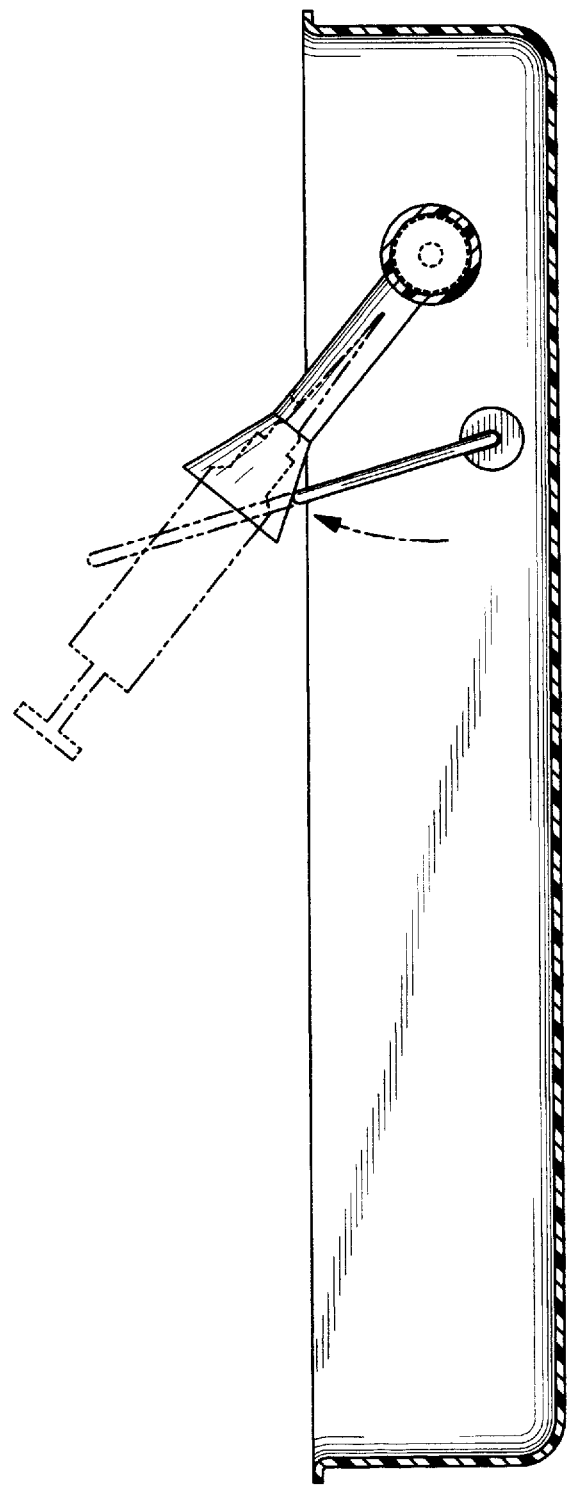

FIG. 2 is a cross-sectional view of the embodiment of FIG. 1.

Figure 3:
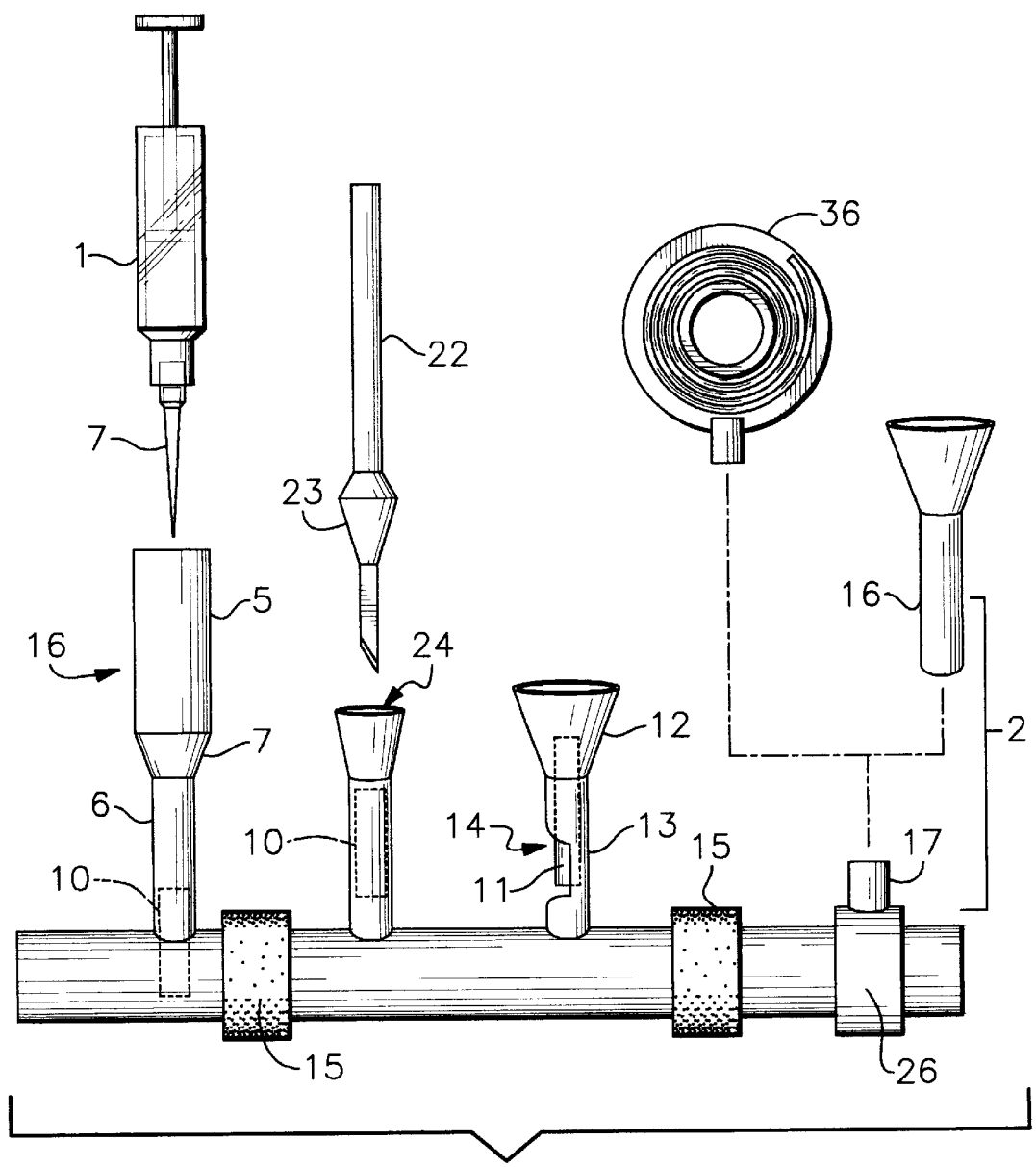

FIG. 3 is a top view showing the holding bar and the attached medical device components.

Figure 4:
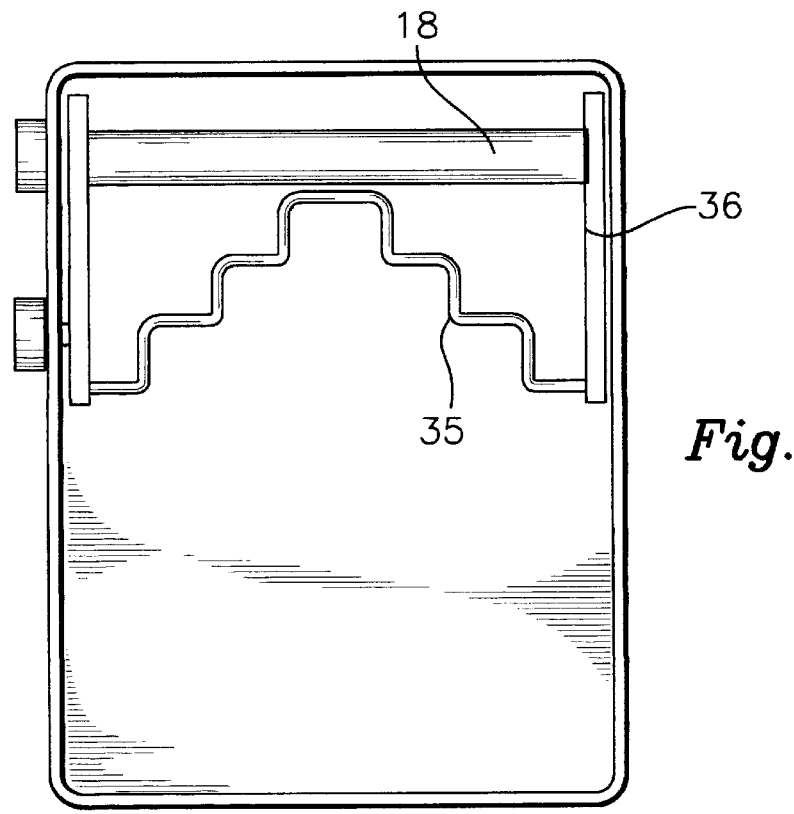

FIG. 4 is a view of a system for joining the bar to the support.

Figure 5:
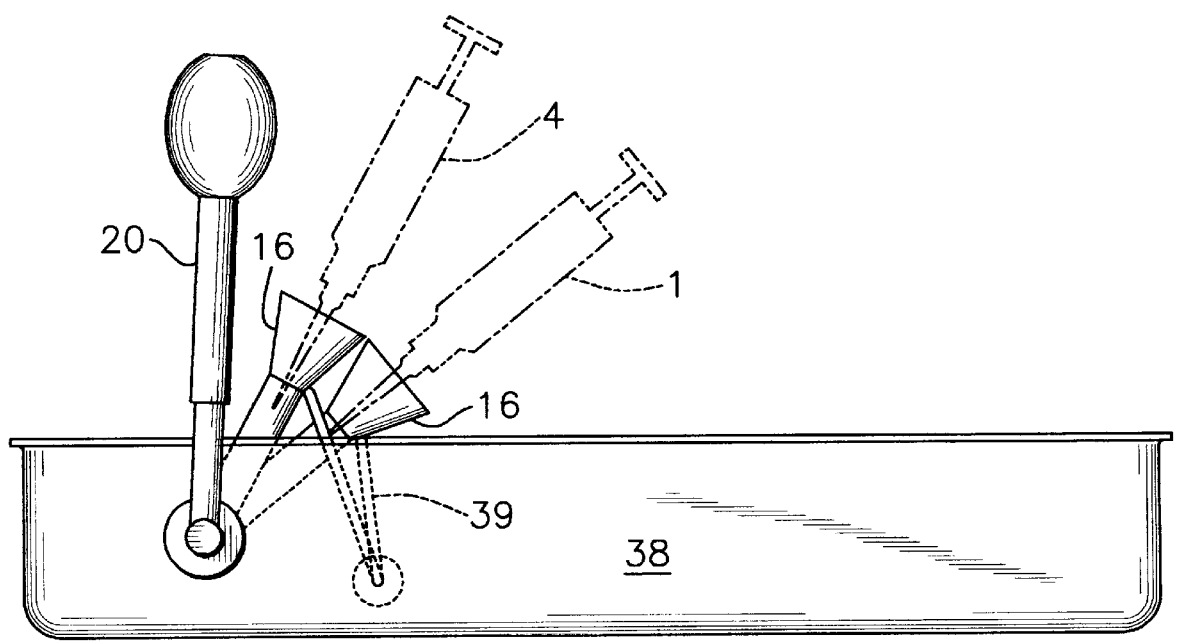

FIG. 5 is a side view of raised medical devices held in raised holders using a bracket-type system.

Figure 6:
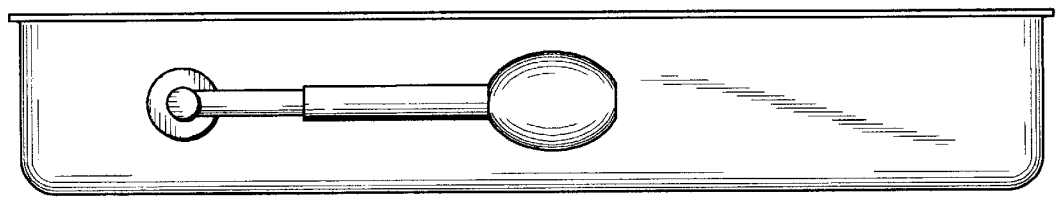

FIG. 6 is a view of the embodiment of FIG. 5 when in the lowered position from the side.

Figure 7:
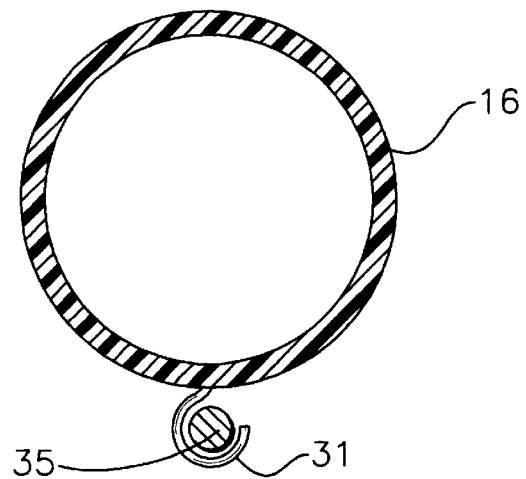

FIG. 7 is a cross sectional view of the connection between the holding bar support and the holding means of FIG. 1.

DETAILED DESCRIPTION OF THE PREFERRED EMBODIMENT

As can best be seen by reference to Figure One the invention is the holder for devices such as a syringe 1 and scalpel 22. Other devices are also commonly held variety of holders and shapes of holders are referred to herein as removable holding means or simply holding means 16.

As can be seen by reference to FIG. 1 and 3, the attachment means 2 is a holding bar 18, which can receive the holding means 16. The holding bar 18 may be hollow so as to define a channel 9 into which antiseptic fluid may be pumped as through an injection tube 8 which is sealed by threads to lure lock syringe 4 having a lure lock 3 fitting to attach to the injection tube 8. Fluid may be held within the chamber of the lure lock syringe 4 and introduced through the tubes. A bulb 21 may be put in place on the hollow tube 8 attached to the bar 18 so that the bulb may be squeezed in order to move the antiseptic fluids in the channel 9 and then up into the holding means 16. A sponge 10 may be within the attachment tube or within the holding means in order to absorb the antiseptic by the sponge provided to prevent the holding means 16 from overflowing.

The syringe 1 has a needle 7. The needle 7 may embedded or run along side the sponge 10 when the sponge 10 is soaked with antiseptic fluid.

The holding means 16 may be comprised of a narrowed section 6 attached to an attachment means 17. As shown in FIG. 3, the holding means 16 may come off of the attachment means 17 so that an alternative item, here a spool 36 may be put in its place. This particular attachment means 17 comprises a cylinder or sleeve 26 which fits around the bar 18 so that the spool 36 does not rotate upward with the other instruments.

In order to maintain the raised position of the holding means when they are rotated upward, a support bar 29 or a series of support bars 29 mounted on one or more support pivots 32 may support individually each of the holding means 16. A catch 31, as shown in FIG. 7, which catch is attached to the holding means 16 may be used in order to grasp, releasably, the support bar 29 and secure the position of the holding means to the support bar.

As opposed to a single support bar 29, a series of individual support bars running up frome of the base of the tray as shown in FIG. 5 may individually support each of the holding means, with or without a catch 31.

The support bar may be a staggered bar as shown in the dotted line in FIG. 1 and as shown in FIG. 4. By having a staggered horizontal support bar, the height of the holding means is staggered at different levels as shown in FIG. 5 where different length individual support bars 29 are used for each separate holding means 16. The horizontal staggering is shown in FIG. 1 as being staggered away from the horizontal bar when the holding means are lowered. FIG. 4 shows the opposite arrangement. In this way, as the support bar is raised, the holding means over it are raised. FIG. 4 shows a belt 36 connecting a rotating support bar pivot to a rotating holding means pivot so that as one is raised, the other rotates upward by virtue of this belt 36 acting as a belt drive.

The staggered horizontal support bar 35 which is mounted on either side to a support bar 29 is rotated upward. This staggered bar 35 then latches each of the hooks 31, if necessary with the aid of the user, and then all of the devices are supported at a separate level which may rise or fall depending on the use desired.

Since, as shown in FIG. 3 it is desirable to have some medical devices remain on the bottom of the tray, the support bar would typically be above these unraised items.

This can be seen by reference to FIG. 3. The holding means 16 may be removable. The holding means 16 contains a holding area 13 which may contain a needle or scalpel cover 11. This also shows an open space 14, a narrowed area of the holding means 16. Through this open space the cover 11 may be held in place while the needle 7 is removed or the needle 7 may be removed with the cover 11 by not holding the cover 11 in place. This open area 14 (which may be defined as a weakened area) might allow the holding means to be broken away so that selected holding means and the sharp items held by them such as the scalpel 22 or syringe 1 with needle 7 may be removed with a cover 11.

This would also be possible where there was removable holding means 16 attached to tube 17. The expanded area 5 has an inner face 24 which serves to securing hold a similarly shaped surface 23 on the scalpel 22. The expanded area is adapted so as to guide the scalpel or syringe which is inserted.

The syringe is shown here having a matching surface 23 which aids in the alignment to the to the holding means. Corresponding shapes or even corresponding colors might be used to match medical devices to the holding means 16 into which they were to be inserted.

Where a staggered design is desirable each of the attachment tubes 17 may be pivotally mounted on sleeve 26 fitting over the holding bar 18 although this would make the use of the channel 9 holding antiseptic more difficult, but washers could be used in extreme cases to make this functional.

Sponges 15 may be put in place in order to absorb fluids, to cushion and further restrict the motion of the bar 9 as it rotates the sponges against the bottom of the tray.

As shown on FIG. 5, a handle 20 may be in place outside of the tray 38 in order to raise and lower the holding means 16. Here, the holding means 16 are held up by individual brackets 39 mounted to the bottom of the tray 38 or mounted to a bar (not shown) which would run along the bottom of the tray. The length of these brackets 39 varies to vary the height of the holding means.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

I claim:

1. A tray for holding medical instruments having a sharp edge comprising:
   a) a tray defining an internal volume having a bottom, a left wall and a right wall on either side of the internal volume;
   b) a receiving means attached to the tray;
   c) at least one holding means for releasably holding the sharp edge of at least one medical instrument attached to the receiving means and wherein the receiving means is detachable from the at least one holding means so that the at least one medical instrument may be retrieved with the sharp edge encased and**wherein the holding means is connected to the receiving means at a point of connection located between the holding means which point by way of a cooperating male and female thread lure lock fastening means located along the point of connection.

2. The invention of claim 1 wherein the holding means further comprises a frictional hold for a sharps cover covering the at least one medical device.

3. A tray for holding medical instruments having a sharp edge comprising:
   a) a tray defining an internal volume having a bottom a left wall and a right wall on either side of the internal volume;
   b) a receiving means attached to the tray;
   c) at least one holding means for releasably holding the sharp edge of at least one medical instrument attached to the receiving means and wherein the tray and receiving means further comprises:
      a) a first wall attached to the tray and a pivoting mount mounted on the first wall;
      b) a first horizontal shaft secured perpendicular to the first wall by the pivoting mount;

c) and wherein the at least one receiving means is mounted to the tray by way of mounting the at least one receiving means on the horizontal shaft.

4. The invention of claim 3 wherein the at least one receiving means pivots around the horizontal shaft so as to raise the receiving means relative to the bottom of the tray.

5. The invention of claim 4 wherein the horizontal shaft mounting is a pivot so that the shaft may pivot relative to the wall and further comprising at least one second receiving means which does not pivot around the shaft.

6. The invention of claim 4 wherein the invention further comprises a retaining bar which may be rotated under the at least one receiving or holding means so as to maintain the height of the holding means relative to the bottom of the tray.

7. The invention of claim 6 wherein the invention comprises at least one second receiving means for holding at least one second holding means and wherein the at least one retaining bar is staggered so as to hold the height of the at least one first holding means at a different height than the at least one second holding means relative to the bottom of the tray.

8. The invention of claim 6 wherein the at least one retaining bar is attached to the bottom of the tray and traveling from the bottom of the tray to the at least one holding means or at least one receiving means.

9. The invention of claim 8 wherein the invention further comprises at least one second retaining bar mounted to the bottom of the tray traveling to at least one second holding means or at least one second receiving means.

10. The invention of claim 9 wherein retaining bar may hold the holding means at more than one height above the bottom of the tray.

11. The invention of claim 9 wherein the at least one second retaining bar holds the at least one second holding means at a height different from the at least one first holding means when both the at least one first holding means and the at least one second holding means are supported on the at least one first retaining bar and the at least one second retaining bar.

12. The invention of claim 6 wherein the rotation of the retaining bar rotates upward the holding means to the desired height.

13. The invention of claim 3 wherein the at least one horizontal shaft mounting is a pivot so that as the horizontal shaft is rotated the horizontal shaft pivots on the pivot relative to the at least one wall.

14. The invention of claim 13 wherein the horizontal shaft further comprises a pivoting shaft and wherein the position of the holding means is substantially fixed to the horizontal shaft and wherein the holding means holds the medical instrument parrallel to the bottom so that as the shaft pivots the holding means is turned upward raising the medical instruments above the bottom.

15. The invention of claim 13 wherein the pivot further comprises a handle having a substantially fixed attachment to the horizontal shaft so that when the handle is rotated the horizontal shaft is rotated raising the level of the holding means.

16. The invention of claim 3 further comprising a bracket means for fixing the position of the holding means relative to the bottom of the tray when the holding means is raised from the bottom of the tray.

17. The invention of claim 16 wherein the position of the holding means is substantially fixed relative to the horizontal shaft by a locking stop.

18. The invention of claim 16 wherein the bracket means further comprises a shaft attachable to the tray said shaft having a length and said shaft being extendable from the tray along the length to the holding means so as to fix the height of the holding means above the tray.

19. The invention of claim 18 wherein the bracket means further comprises at least one second bracket and wherein the holding means further comprises at least one second holding means and wherein the location of the first holding means is staggered relative to the position of the second holding means when both bracket means are mounted to the tray and holding means to fix the height of the holding means above the tray.

20. The invention of claim 16 wherein the shaft further comprises a handle accessible by the user attached to the shaft to allow the user to raise the shaft to a desired location.

21. The invention of claim 16 wherein the bracket means further comprises the mounting of the horizontal bar to the tray at least one tray wall with a frictionally fixable pivot.

22. The invention of claim 21 wherein there are discrete points of increased frictional control so as to allow for the angle of the holding means from the tray at discriminate angles.

23. The invention of claim 16 further comprising a marking means for identifying the medical instrument with the corresponding receiving means.

24. The invention of claim 23 wherein the holding means defines and face and wherein the marking means is a color on the face of the holding means corresponding to the color of the medical device.

25. The invention of claim 23 wherein the holding means comprises a face having a face shape and wherein the marking means comprises having a medical device face on the medical device which cooperates to create a better fit with the face of the medical holding means.

26. The invention of claim 1 wherein the holding means further comprises a first holding part and a second holding part and wherein the first holding part covers the sharp portion of the medical instrument and is in turn removably attached to the second holding part which is, in turn connected to the receiving means.

27. The invention of claim 1 wherein the receiving means is removable with the holding means from the tray.

* * * * *